(12) United States Patent
Kimata et al.

(10) Patent No.: US 8,058,592 B2
(45) Date of Patent: Nov. 15, 2011

(54) CERAMIC HEATER, GAS SENSOR, AND METHOD OF PRODUCING CERAMIC HEATER

(75) Inventors: Takehito Kimata, Kariya (JP); Kiyomi Kobayashi, Kuwana (JP)

(73) Assignee: Denso Corporation, Kariya (JP)

(*) Notice: Subject to any disclaimer, the term of this patent is extended or adjusted under 35 U.S.C. 154(b) by 753 days.

(21) Appl. No.: 12/054,826

(22) Filed: Mar. 25, 2008

(65) Prior Publication Data

US 2008/0237065 A1 Oct. 2, 2008

(30) Foreign Application Priority Data

Mar. 27, 2007 (JP) ................. 2007-082586
Jan. 25, 2008 (JP) ................. 2008-015160

(51) Int. Cl.
*H05B 3/02* (2006.01)
*B32B 9/00* (2006.01)

(52) U.S. Cl. ........ 219/538; 219/522; 219/547; 219/203; 219/209; 209/794.5; 204/431; 428/472; 428/697; 428/698; 428/699; 428/418; 428/458; 428/469

(58) Field of Classification Search ................. 219/538, 219/522, 547, 203, 209; 205/794.5; 204/431; 428/472, 697–699, 418, 458, 469
See application file for complete search history.

(56) References Cited

U.S. PATENT DOCUMENTS 5,493,102 A 2/1996 Takase et al.
5,750,267 A * 5/1998 Takase et al. ................. 428/469

FOREIGN PATENT DOCUMENTS

| EP | 1 696 704 | 8/2006 |
|---|---|---|
| JP | 05-101972 | 4/1993 |
| JP | 06-283261 | 10/1994 |
| JP | 06-290856 | 10/1994 |
| JP | 07-114979 | 5/1995 |
| JP | 10-206373 | 8/1998 |
| JP | 2000-048939 | 2/2000 |
| JP | 2005-158471 | 6/2005 |
| JP | 2006-91009 | 4/2006 |
| JP | 2006-091009 | * 4/2006 |
| JP | 2006-208140 | 8/2006 |

OTHER PUBLICATIONS

Japanese Office Action dated May 26, 2009, issued in corresponding Japanese Application No. 2008-015160 with English Translation.
Japanese Office Action dated Nov. 25, 2008 issued in corresponding Japanese Application No. 2008-015160 with English Translation.
Japanese Office Action dated Feb. 8, 2011, issued in corresponding Japanese Application No. 2008-015160 with English Translation.

* cited by examiner

*Primary Examiner* — Shawntina Fuqua
(74) *Attorney, Agent, or Firm* — Nixon & Vanderhye PC

(57) ABSTRACT

A gas sensor is equipped with a built-in ceramic heater. The gas sensor detects the concentration of a predetermined gas component contained in the exhaust gas. The ceramic heater has a heater base member made of ceramic, a heating element formed in the inside of the heater base material, and a pair of external electrode pads that is electrically connected to the output terminals for the outer leads. The external electrode pads, the heating element, and the heater leads are made of base metal. The outer surface of each external electrode pad is covered only with a dense protective film made of noble metal such as gold (Au), silver (Ag), platinum (Pt), rhodium (Rh), and palladium (Pd).

6 Claims, 11 Drawing Sheets

CERAMIC HEATER, GAS SENSOR, AND METHOD OF PRODUCING CERAMIC HEATER

CROSS-REFERENCE TO RELATED APPLICATION

This application is related to and claims priority from Japanese Patent Applications No. 2007-82586 filed on Mar. 27, 2007 and No. 2008-15160 filed on Jan. 25, 2008, the contents of which are hereby incorporated by reference.

BACKGROUND OF THE INVENTION

1. Field of the Invention

The present invention relates to a ceramic heater which is built into a gas sensor capable of detecting the concentration of a specific gas component contained in a target gas to be measured, for example, the exhaust gas which is emitted from the internal combustion engine mounted to motor vehicles. The present invention further relates to a gas sensor equipped with the above ceramic heater, and to a method of producing the above ceramic heater.

2. Description of the Related Art

FIG. 10 is the sectional diagram of the conventional gas sensor 8 equipped with the built-in ceramic heater 9 in its axial direction. As shown in FIG. 10, the gas sensor 8 is capable of detecting the concentration of the specific gas (such as the oxygen concentration) contained in the exhaust gas emitted from the internal combustion engine mounted to the motor vehicle. The gas sensor 8 has the built-in the ceramic heater 9 and the gas sensor element 80. The ceramic heater 9 heats the gas sensor element 80.

The ceramic heater 9 has the heater base member 910 made of ceramic. The heater base member 910 has the heater element (omitted from FIG. 10) therein.

FIG. 11 is the cross section of the contact area between the external electrode pad 912 and the output terminal in the conventional ceramic heater 9 built in the gas sensor 8 shown in FIG. 10. As shown in FIG. 11, the external electrode pad 912 is formed on an outer surface of the heater base member 910. The external electrode pad 912 is electrically connected to the heater element in the gas sensor 8.

The external electrode pad 912 is made of tungsten (W). The outer surface of the external electrode pad 912 is covered with the protective film 914 formed by a nickel plating film, for example. Japanese patent laid open publication No. 2005-158471 has disclosed a gas sensor having such a construction.

As shown in FIG. 11, the protective film 914 is electrically connected to the external lead 92 by the brazing member 915 made of Au—Cu alloy, for example. This structure allows the external electrode pad 912 to have thermal resistance properties and to resist oxidation.

As shown in FIG. 10, the gas sensor element 80 is of a cylindrical shape, in the bottom part of the diagram. The gas sensor 8 further has the housing in which the cylindrical gas sensor element 80 is disposed, and the ceramic heater 9 is disposed in the gas sensor element 80.

The gas sensor 8 has the target gas measurement chamber 82 and the atmosphere gas chamber 83. In actual use, the front end outer peripheral surface of the gas sensor element 80 is directly exposed to the target gas introduced into the target measurement gas chamber 82. The inner periphery surface of the gas sensor element 80 is exposed to atmosphere air introduced into the atmosphere chamber 83. The external electrode pad 912 is exposed to the atmosphere air in the atmosphere chamber 83.

The target gas measurement chamber 82 and the atmosphere chamber 83 are sealed with the seal member 84 placed between the gas sensor element 80 and the housing 81. This structure protects the atmosphere chamber 83 from entry of the exhaust gas.

However, because the exhaust gas temperature increases according to recently strict automobile emissions control, there is a possibility of applying thermal load to the seal member 82, and as a result, the air-tightness capability between the target gas measurement chamber 82 and the atmosphere chamber 83 decreases. This could allow entry of the exhaust gas into the atmosphere chamber 83, and as a result, there is a possibility that corrosive components (such as nitrogen oxide) contained in the exhaust gas reaches the protective film 914.

As described above, because the protective film 914 is made of a nickel (Ni) plating film and the like, nickel (Ni) easily reacts with such a corrosive component, nitric acid that is generated from nitrogen oxide contained in the exhaust gas. Accordingly, there is a possibility that the nickel (Ni) component in the protective film 914 is corroded by nitrogen oxide.

On the other hand, as shown in FIG. 11, there is another technique to cover the outer peripheral surface of the protective film 914 and the brazing member 915 with a chromium (Cr) plating film. However, thermal stress can cause cracks in the Cr plating film that is applied to the brazing member 915. Corrosive components enter cracks generated in the Cr plating film, and finally reach the protective film 914 that is made of nickel (Ni). This corrodes the protective film 914.

FIG. 12 shows a cross section of the contact area of another construction between the external electrode pad 912 and an output terminal 920 in the conventional ceramic heater shown in FIG. 10.

As shown in FIG. 12, Japanese patent laid open publication No. JP 2006-91009 has proposed a structure to connect the external lead to the external electrode pad 912 with the output terminal 920, not to fix them through a brazing member. The output terminal 920 is a part capable of supporting the base end part of the ceramic heater 9 in its thickness direction. In the ceramic heater having the construction shown in FIG. 12, the external electrode pad 912 is covered with the primary protective film 916 made of a Ni plating film and further covered with the secondary protective film 917 made of a gold (Au) plating film in order to keep its corrosion resistance.

However, one or more pin holes are often formed in the secondary protective film 917 made of the Au plating film. The presence of the pin holes in the secondary protective film 917 causes a possibility that the corrosive components enter and finally reach the primary protective film 916 through the pin holes. This often causes corrosion of the primary protective film 916 made of a nickel (Ni) film.

For this reason, there is strong demand of obtaining a ceramic heater equipped with an external electrode pad with superior anti-corrosion and thermal resistance.

SUMMARY OF THE INVENTION

It is an object of the present invention to provide a ceramic heater with superior anti-corrosion and anti-thermal stress properties. It is another object of the present invention to provide a gas sensor equipped with the ceramic heater, and to further provide a method of producing the ceramic heater.

To achieve the above purposes, the present invention provides a ceramic heater that is built in a gas sensor capable of detecting the concentration of a specific gas component contained in the target gas to be measured. The ceramic heater has a heater base member, a heating element, and a pair of heater leads. The heater base member is made of ceramic. The heating element is formed in the inside of the heater base member. Each external electrode pad is formed at the outer surface of the heater base member and electrically connected to the corresponding output terminal of the outer lead. The heating element is electrically connected to the pair of external electrode pads through the pair of heater leads. In the ceramic heater, the external electrode pads, the heating element, and the heater leads are made of base metal. At least a part of the outer surface of each external electrode pad is covered only with a dense protective film made of noble metal.

The present invention has following action and effects. The protective film is made only of a noble metal. The protective film is formed using such material with superior corrosion resistance. This structure of the ceramic heater can protect the pair of external electrode pads from corrosion even when exposed to the exhaust gas emitted from the internal combustion engine of the motor vehicle. Thereby, the present invention can provide the ceramic heater with superior corrosion resistance.

Further, at least a part of the outer surface of each external electrode pad is covered with the dense protective film made only of noble metal with superior thermal resistance. The area at which each external electrode pad is substantially and electrically connected to the corresponding output terminal is covered with the protective film. This structure can protect the area of the external electrode pads made of base metal from direct exposure to the exhaust gas of high temperature. It is thereby possible to protect the external electrode pads from heat deterioration and oxidation. As a result, the present invention can provide the ceramic heater with superior thermal resistance capability.

As described above, according to the present invention, it is possible to provide the ceramic heater with superior corrosion resistance and superior thermal resistance.

In accordance with another aspect of the present invention, there is provided a ceramic heater that is built in a gas sensor capable of detecting the concentration of a specific gas component contained in the target gas to be measured. The ceramic heater has a heater base member, a heating element, and a pair of heater leads. The heater base member is made of ceramic. The heating element is formed in the inside of the heater base member. Each external electrode pad is formed at the outer surface of the heater base member and electrically connected to the corresponding output terminal of the outer lead. The heating element is electrically connected to the pair of external electrode pads through the pair of heater leads. In the ceramic heater, the external electrode pads, the heating element, and the heater leads are made of base metal. In particular, at least a part of the outer surface of each external electrode pad is covered only with a protective layer. The protective layer is made of a dense protective film made of noble metal and a dense protective film made of chromium (Cr).

In the ceramic heater according to the present invention, at least a part of the outer surface of each external electrode pad is covered only with a protective layer and the protective layer is made of a dense protective film made of noble metal and a dense protective film made of chromium (Cr). That is, at least the part of the outer surface of each external electrode pad is coated with the chromium (Cr) film and the noble metal film with superior corrosion resistance and thermal resistance. Because this chromium (Cr) component in the chrome film becomes chromium oxide, the chrome (Cr) film forms a passive state film on the surface of the protective film. Similar to the ceramic heater previously discussed, the present invention can provide the ceramic heater with superior corrosion resistance and thermal resistance properties.

As described above, according to the present invention, it is possible to provide the ceramic heater with superior corrosion resistance and thermal resistance properties.

In accordance with another aspect of the present invention, there is provided a method of producing a ceramic heater. The ceramic heater is built into a gas sensor capable of detecting the concentration of a specific gas component contained in the target gas to be measured. The ceramic heater is comprised of the heater base member, the heating element, the pair of external electrode pads, and the pair of heater leads. In the method of producing the ceramic heater, noble-metal plating is carried out to form the protective film made of noble metal on at least a part of the outer surface of each external electrode pad, and thermal treatment for the protective film made by means of the noble metal plating is performed at not less than a temperature which is lower than the melting point of the noble metal by 150° C.

In the method of producing the ceramic heater, the heat treatment is carried out for the noble metal plating film at a temperature that is lower than the melting point of the noble metal by 150° C. It is thereby possible to produce the ceramic heater with superior corrosion resistance and thermal resistance properties. That is, after performing the noble metal plating for the pair of external electrode pads, the heat treatment is performed for the noble metal plating film in order that noble metal softens and is adequately workable to make a slightly rough surface. It is therefore possible to increase adhesion force generated between the pair of external electrode pads and the protective film based on the Anchor effect. Accordingly, the present invention can provide the method of producing a ceramic heater with superior corrosion resistance and thermal resistance properties.

In accordance with another aspect of the present invention, there is provided a ceramic heater. In particular, at least a part of the outer surface of each external electrode pad is covered only with a dense protective film made of chromium (Cr). That is, the protective film is made of chromium (Cr). Such a chromium (Cr) film becomes chromium oxide at the surface of the protective film and the chromium oxide forms a passive film. This can provide a protective film with superior corrosion resistance. As a result, it is possible to protect the external electrode pads from corrosion even if exposed to exhaust gas. Thus, the present invention provides the ceramic heater with superior corrosion resistance.

Further, at least a part of the outer surface of each external electrode pad is covered with a protective film made only of chromium (Cr). Chromium (Cr) has superior thermal resistance properties. Because the part of each external electrode pad which is substantially connected to the output terminal is covered with the protective film, this can protect the external electrode pads made of base metal from direct exposure to the high temperature exhaust gas, and protect the external electrode pads from thermal deterioration and oxidation. As a result, the present invention can provide the ceramic heater with superior thermal resistance.

In accordance with another aspect of the present invention, there is provided a ceramic heater. In the ceramic heater, at least the pair of external electrode pad is made only of noble metal. That is, because each external electrode pad is made only of material with superior corrosion resistance, it is possible to protect the external electrode pads from corrosion even if exposed to the exhaust gas. The present invention thereby provides the ceramic heater with enhanced corrosion resistance.

Further, because the external electrode pads are made of noble metal with superior thermal resistance, it is possible to protect the external electrode pads from thermal deterioration even if exposed to the high temperature exhaust gas. As a result, it is possible to provide the ceramic heater with superior thermal resistance. Thus, the present invention provides the ceramic heater with enhanced corrosion resistance and superior thermal resistance.

In accordance with another aspect of the present invention, there is provided a ceramic heater to be built into a gas sensor. The gas sensor is capable of detecting the concentration of a specific gas component contained in the target gas to be measured. The ceramic heater has the heater base member, the heating element, and the pair of heater leads. The heater base member is made of ceramic. The heating element is formed in the inside of the heater base member. Each external electrode pad is formed at the outer surface of the heater base member and electrically connected to the corresponding output terminal of the outer lead. The heating element is electrically connected to the pair of external electrode pads through the pair of heater leads. In the ceramic heater, the heating element, and the heater leads are made of base metal. In particular, each external electrode pad is made of chromium (Cr).

Because each external electrode pad is made of chromium (Cr), a passive state film made of chromium oxide is formed at the surface of each external electrode pad. The passive state film can protect each external electrode pad from corrosion even if exposed to an exhaust gas. It is thereby possible to provide the ceramic heater with superior corrosion resistance.

Still further, because chromium oxide has superior thermal resistance properties, the formation of the chromium oxide can prevent the external electrode pads from thermal deterioration. As a result, it is possible to provide the ceramic heater with superior thermal resistance. Accordingly, the present invention can provide the ceramic heater with superior corrosion resistance and thermal resistance.

In accordance with another aspect of the present invention, there is provided a gas sensor that is equipped with the ceramic heater according to the present invention having the features previously discussed. The ceramic heater is built into the gas sensor. The present invention provides the gas sensor with high reliability.

It is further preferable to form the protective layer made of one of or a combination of silica and ceramic on a part of the external electrode pad when such a part is not covered with the protective layer.

It is preferable that noble metal is at least one or more of gold (Au), silver (Ag), platinum (Pt), rhodium (Rh), and Palladium (Pd). This case can form the protective film with superior corrosion resistance and thermal resistance.
As a result, it is possible to obtain the ceramic heater with more superior corrosion resistance and thermal resistance.

It is preferable that the entire outer surface of each external electrode pad is covered with the protective film. This can protect the entire of the external electrode pads from corrosion and thermal deterioration.

It is possible that the external electrode pads, the heating element, and the heater leads are made of tungsten (W). This can provide the ceramic heater with superior corrosion resistance at low manufacturing cost.

It is preferable to perform thermal treatment at a temperature of not less than the melting point of the noble metal.

Because the heat treatment can soften the noble metal plating film, it is possible to be more adequately work it onto the external electrode pad. As a result, it is possible to increase the adhesion force between the external electrode pads and the protective film.

It is preferable that each of the external electrode pads is made of at least one of gold (Au), silver (Ag), platinum (Pt), rhodium (Rh), and palladium (Pd). This can provide the external electrode pad with superior corrosion resistance and thermal resistance. As a result, the present invention can provide the ceramic heater with more superior corrosion resistance and thermal resistance.

It is also preferable that the heating element and the heater leads are made of tungsten (W). This can provide the ceramic heater with superior corrosion resistance at low manufacturing cost.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1:
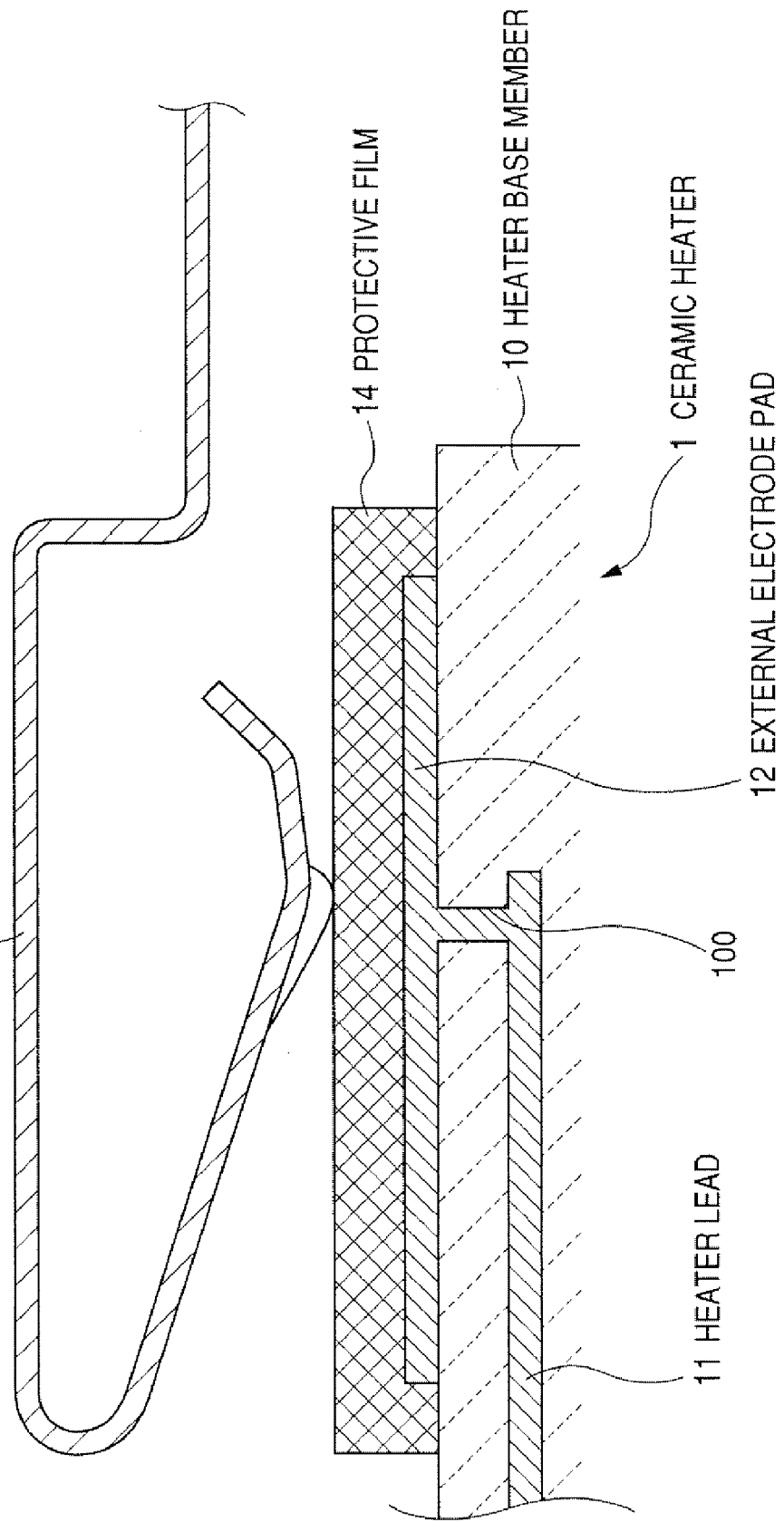
FIG. 1 shows a cross section of the contact area between the external electrode pad and the output terminal in the ceramic heater in its axial direction according to a first embodiment of the present invention.

Hereinafter, various embodiments of the present invention will be described with reference to the accompanying drawings. In the following description of the various embodiments, like reference characters or numerals designate like or equivalent component parts throughout the several diagrams.

First Embodiment

A description will be given of the ceramic heater according to the first embodiment of the present invention with reference to FIG. 1 to FIG. 3.

FIG. 1 shows the cross section of the contact area between the external electrode pad 12 and the output terminal 2 in the ceramic heater 1 in its axial direction according to the first embodiment. FIG. 2 is a front diagram of the ceramic heater 1 according to the first embodiment shown in FIG. 1. FIG. 3 is a side diagram of the base end part of the ceramic heater 1 according to the first embodiment, observed from a different position at 90° of angle from the diagram shown in FIG. 2.

The ceramic heater 1 according to the first embodiment of the present invention is built in the gas sensor. For example, the gas sensor detects the concentration of a specific gas component contained in the exhaust gas which is emitted from the internal combustion engine mounted to the motor vehicle.

As shown in FIG. 1, the ceramic heater 1 is comprised of the heater base member 10 made of ceramic, the heating element (omitted from diagrams), the pair of external electrode pads 12, and the pair of heater leads 11. FIG. 1 shows one external electrode pad 12 and one heater lead 11. The heating element is formed in the inside of the heater base member 10. Each external electrode pad 12 is disposed on the outer peripheral surface of the heater base member 10 and electrically connected to the corresponding output terminal 2 for the external lead (not shown). Each external electrode pad 12 is electrically connected to the heating element through the corresponding heater lead 11.

As shown in FIG. 1, the entire outer surface of each external electrode pad 12 is covered with the protective film 14 made of a dense Gold (Au)-plating film.

For example, the heater base member 10 is made of alumina ($Al_2O_3$) or silicon nitride ($Si_3N_4$). As shown in FIG. 2, the ceramic heater has a cylindrical shape.

The pair of output terminals 2, the heating element, and the pair of heater leads 11 are made of base metal such as tungsten (W).

The through hole 100 is formed between each heater lead 11 and the corresponding external electrode pad 12 in the heater base member 10. The through hole 100 is filled with tungsten (w) that electrically connects the heater lead 11 and the corresponding external electrode pad 12. A current flows from the external electric power source (omitted from drawings) into the ceramic heater 1 in the gas sensor through the pair of output terminals 2. The current then flows into the heating element in the ceramic heater 1 through the pair of protective films 14, the pair of external electrode pads 12, and the pair of heater leads 11. The through hole 100 is formed every combination of the heater lead 11 and the corresponding external electrode pad 12. That is, the pair of through holes 100 is formed in the heater base member 10 in the ceramic heater 1 because the ceramic heater 1 has the pair of heater leads and the pair of external electric pads 12.

Figure 2:
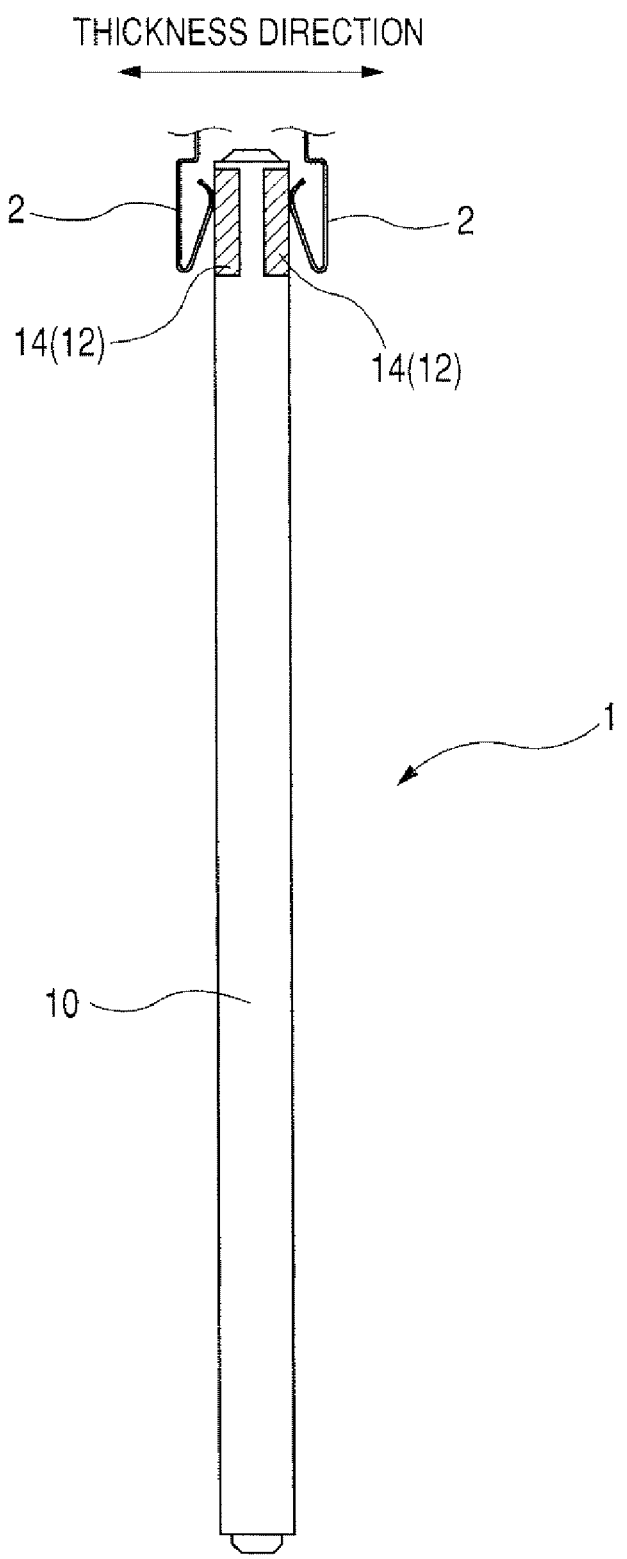
FIG. 2 is a front diagram of the ceramic heater according to the first embodiment shown in FIG. 1.
Figure 3:
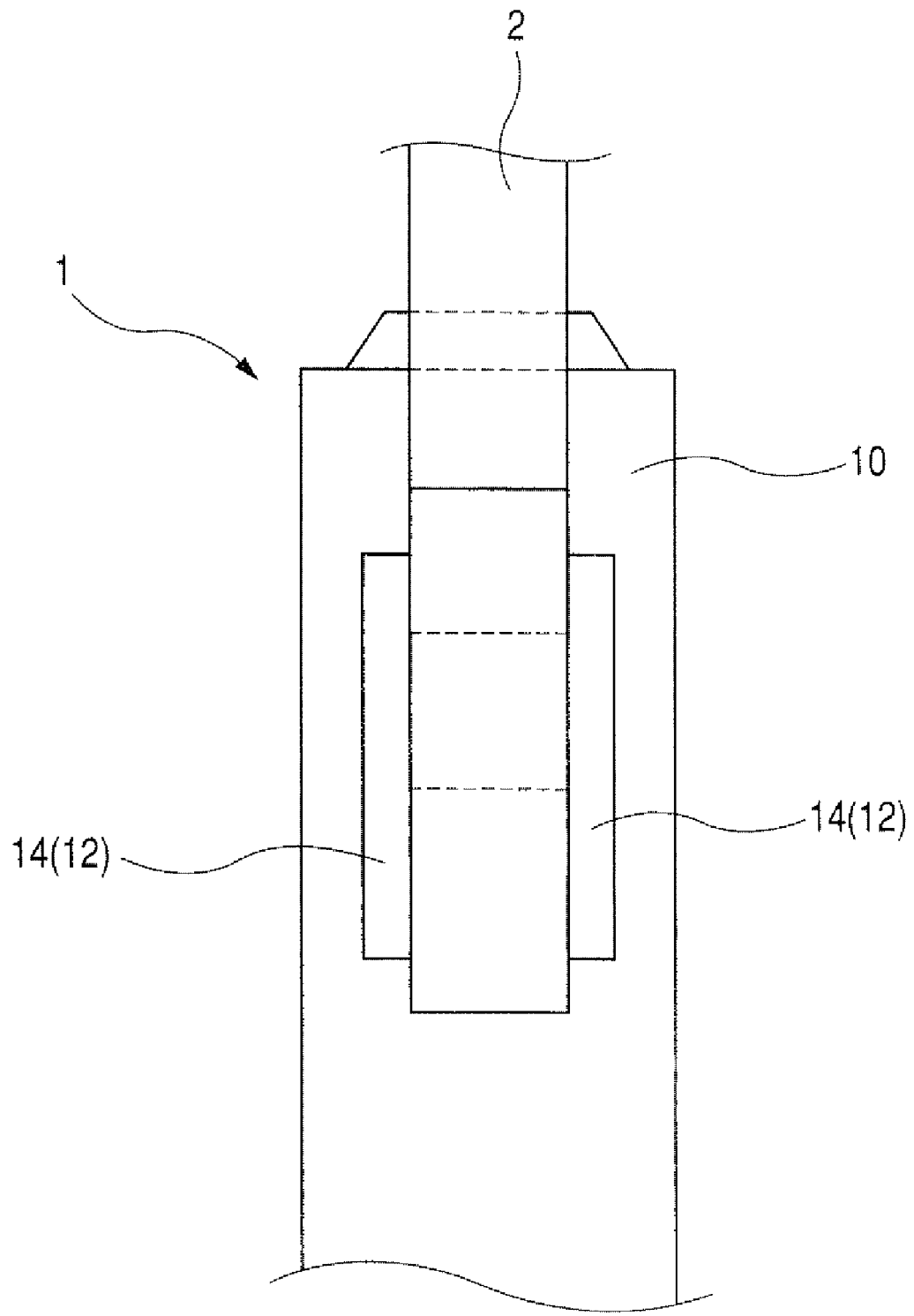
FIG. 3 is a side diagram of the base end part of the ceramic heater according to the first embodiment observed from a different position at 90° of angle from the diagram shown in FIG. 2.

As shown in FIG. 2 and FIG. 3, the pair of output terminals 2 forcedly pushes the base end part of the ceramic heater 1 in its thickness direction.

Figure 11:
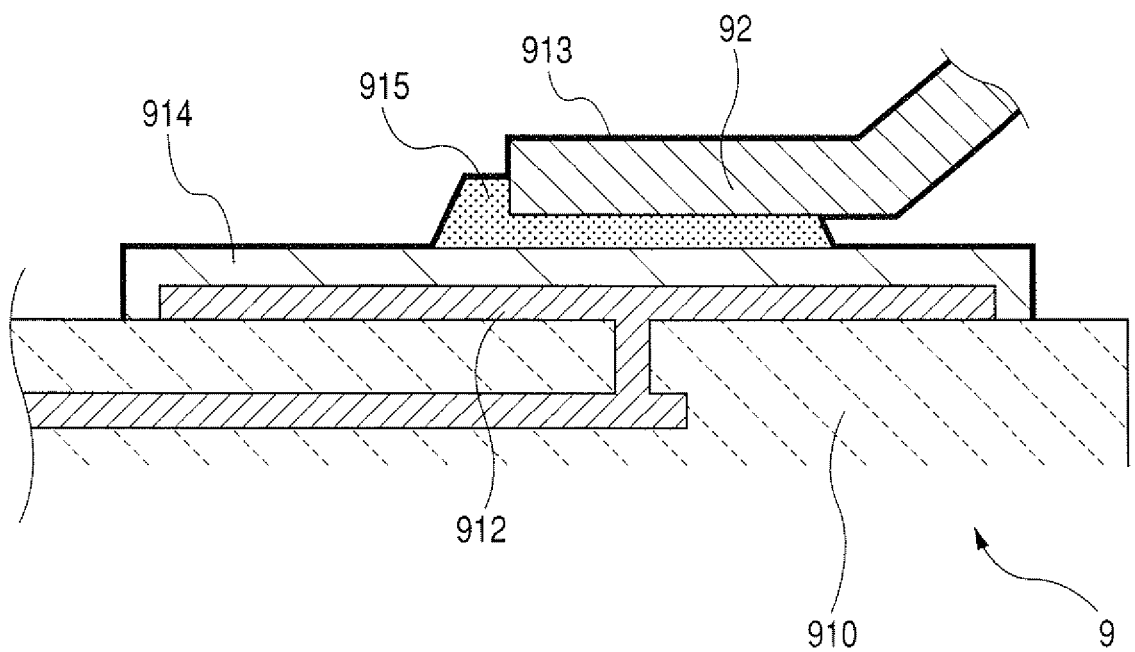
FIG. 11 is a cross section of the conventional ceramic heater which is built in the gas sensor shown in FIG. 10, in particular, shows the contact area between the external electrode pad and the output terminal in the conventional ceramic heater.
Figure 12:
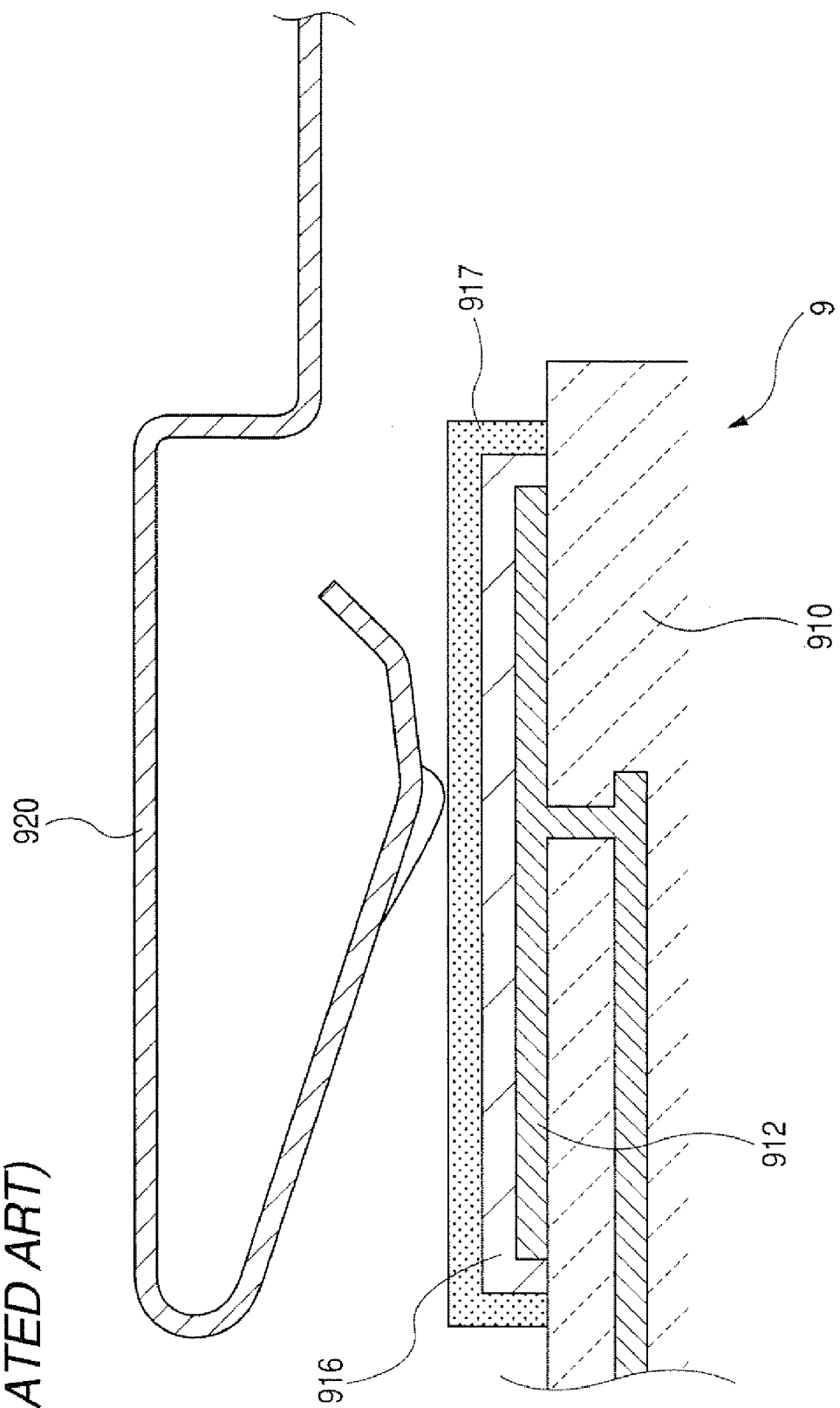
FIG. 12 shows a cross section of the contact area of another configuration between the external electrode pad and the output terminal in the conventional ceramic heater shown in FIG. 10.

Each output terminal 2 is connected to the corresponding external electrode pad 12 through the corresponding protective film 14. That is, in the ceramic heater 1 according to the first embodiment, each external electrode pad 12 is electrically connected to the corresponding output terminal 2 without brazing. (For example, the brazing part is designated by reference number 915 shown in FIG. 11.)

Next, a description will now be given of the actions and effects of the ceramic heater 1 according to the first embodiment of the present invention.

The protective film 14 is made only of gold (Au). It is therefore possible to form the protective film 14 using superior anti-corrosion material. This enables the ceramic heater 1 of the first embodiment to protect a pair of the external electrode pads 12 from corrosion even if exposed to the exhaust gas.

The entire outer peripheral surface of each external electrode pad 12 is covered only with the protective film 14 made of a dense gold (Au) film with superior thermal resistance. This structure can protect the pair of external electrode pads 12 from direct exposure of the high temperature exhaust gas, and thereby protects a pair of the external electrode pads 12 from thermal deterioration and oxidation. As a result, the present invention can provide the ceramic heater 1 with superior thermal resistance.

In particular, in the ceramic heater 1 according to the first embodiment shown in FIG. 1, because the outer peripheral surface of each external electrode pad 12 is covered with the protective film 14 made of gold (Au), it is possible to protect the external electrode pads 12 from corrosion and thermal deterioration when compared with conventional various types of ceramic heaters.

As described above, according to the first embodiment of the present invention, it is possible to provide the ceramic heater with superior corrosion resistance and superior thermal resistance.

Although the pair of protective films 14 is made of a gold (Au) film in the first embodiment described above, it is possible to use a protective film made of another noble metal such as Ag, Pt, Rh, and Pd, instead of the gold (Au) film.

Still further, the protective film can be formed using chromium (Cr). Chromium (Cr) becomes chromium oxide. The chromium oxide forms a passive film. This can protect the external electrode pads 12 from corrosion even if exposed to an exhaust gas. It is thereby possible to provide the ceramic heater with superior corrosion resistance. Because each external electrode pad 12 is covered with the protective film made of chromium (Cr), and chromium (Cr) has superior thermal resistance property, it is thereby possible to protect the external electrode pads 12 from thermal deterioration and oxidation.

Second Embodiment

A description will be given of the ceramic heater 1-1 according to the second embodiment of the present invention with reference to FIG. 4.

Figure 4:
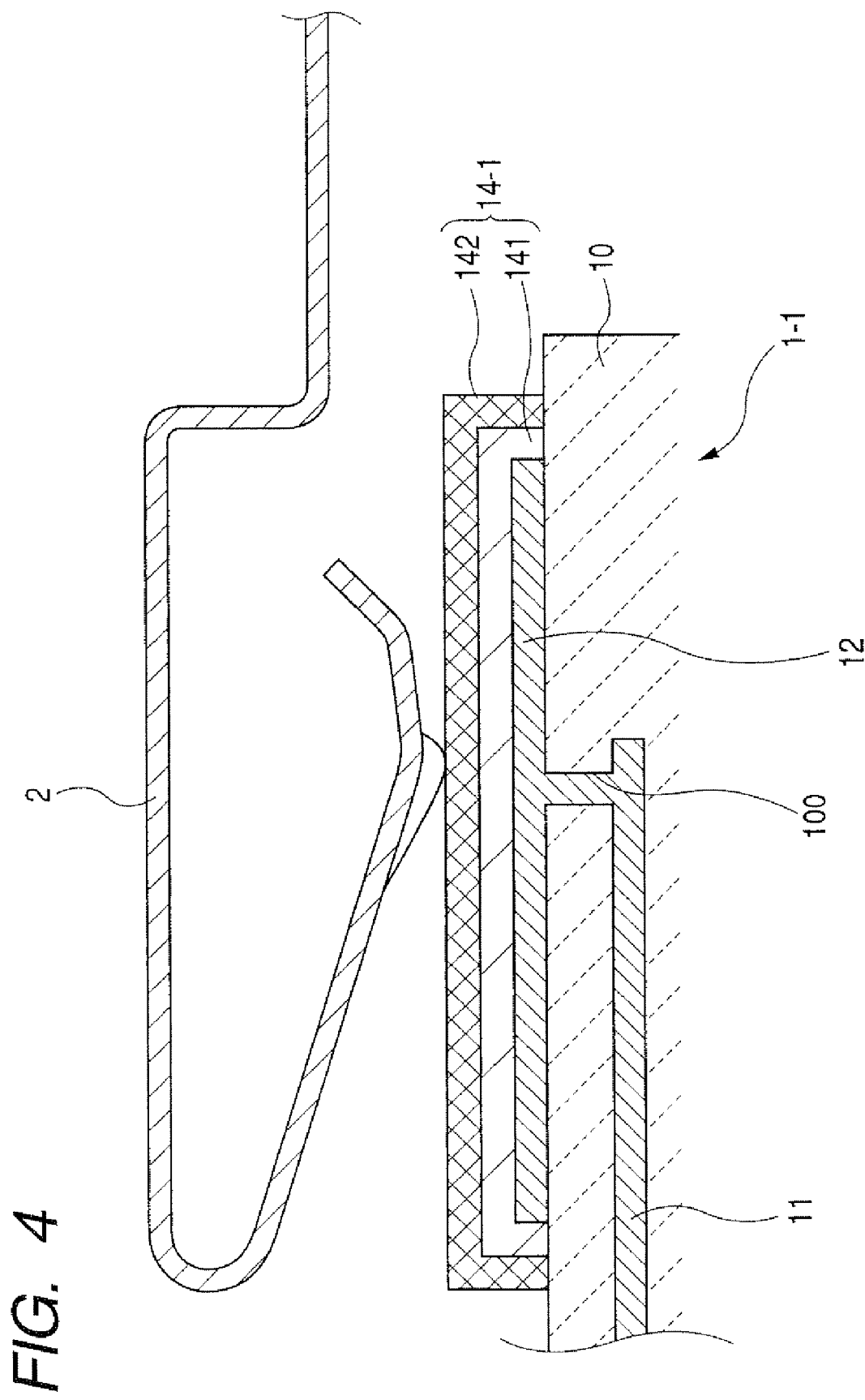
FIG. 4 shows a cross section of the contact area between the external electrode pad and the output terminal in the ceramic heater in its axial direction according to a second embodiment of the present invention.

FIG. 4 shows the cross section of the contact area between the external electrode pad 12 and the output terminal 2 in the ceramic heater 1-1 along its axial direction according to the second embodiment.

In the ceramic heater 1-1 shown in FIG. 4, each protective film 14-1 is a stacked (or lamination) configuration composed of the primary protective film 141 and the secondary protective film 142. The entire outer peripheral surface of each external electrode pad 12 is covered with the primary protective film 141. The primary protective film 141 is covered with the secondary protective film 142.

The primary protective film 141 and the secondary protective film 142 are made of different materials selected from noble metal such as gold (Au), silver (Ag), platinum (Pt), rhodium (Rh), and Palladium (Pd) so that the primary protective film 141 is different in material from the secondary protective film 142. It is possible to form the protective film 14-1 by means of the above structure.

Still further, it is possible to form the protective film 14-1 made of a combination of Cr and the above noble metal. In this case, it is preferable to form the secondary protective film 142 with Cr.

Other components of the second embodiment have the same configuration, action, and effects of those in the ceramic heater according to the first embodiment shown in FIG. 1 to FIG. 3. The explanation for the same components is omitted here.

Third Embodiment

A description will be given of the ceramic heater 1-2 according to the third embodiment of the present invention with reference to FIG. 5.

Figure 5:
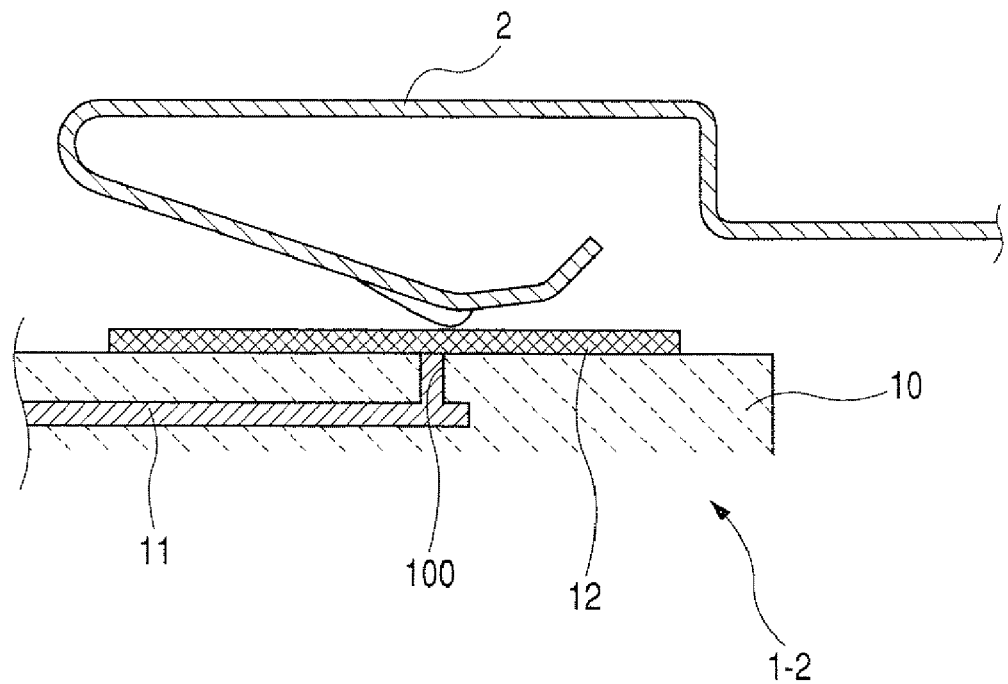
FIG. 5 shows a cross section of the contact area between the external electrode pad and the output terminal in the ceramic heater in its axial direction according to a third embodiment of the present invention.

FIG. 5 shows the cross section of the contact area between the external electrode pad 12 and the output terminal 2 in the ceramic heater 1-2, along its axial direction according to the third embodiment.

The pair of external electrode pads 12 is made of at least one or more of noble metal such as gold (Au), silver (Ag), platinum (Pt), rhodium (Rh), and Palladium (Pd). Other components of the third embodiment have the same configuration, action, and effects of those in the ceramic heater according to the first embodiment shown in FIG. 1 to FIG. 3. The explanation for the same components is omitted here.

Each external electrode pad 12 is made of noble metal. That is, because each external electrode pad 12 is made only of superior anti-corrosion material, it is possible to protect the pair of external electrode pad 12 from corrosion. The present invention can therefore provide the ceramic heater 1-2 with superior corrosion resistance. Further, because each external electrode pad 12 is made of noble metal with superior corrosion resistance, it is possible to halt the progress of thermal deterioration in the external electrode pads 12. As a result, it is possible to provide the ceramic heater 1-2 with superior thermal resistance.

Other components of the third embodiment have the same configuration, action, and effects of those in the ceramic heater according to the first embodiment shown in FIG. 1 to FIG. 3. The explanation for the same components is omitted here.

Although the pair of external electrode pads 12 in the ceramic heater 1-2 according to the third embodiment is made of noble metal, it is acceptable to use a pair of external electrode pads made of chromium (Cr). This structure can provide the ceramic heater with adequately-superior corrosion resistance and thermal resistance.

Fourth Embodiment

A description will be given of the ceramic heater 1-3 according to the fourth embodiment of the present invention with reference to FIG. 6.

Figure 6:
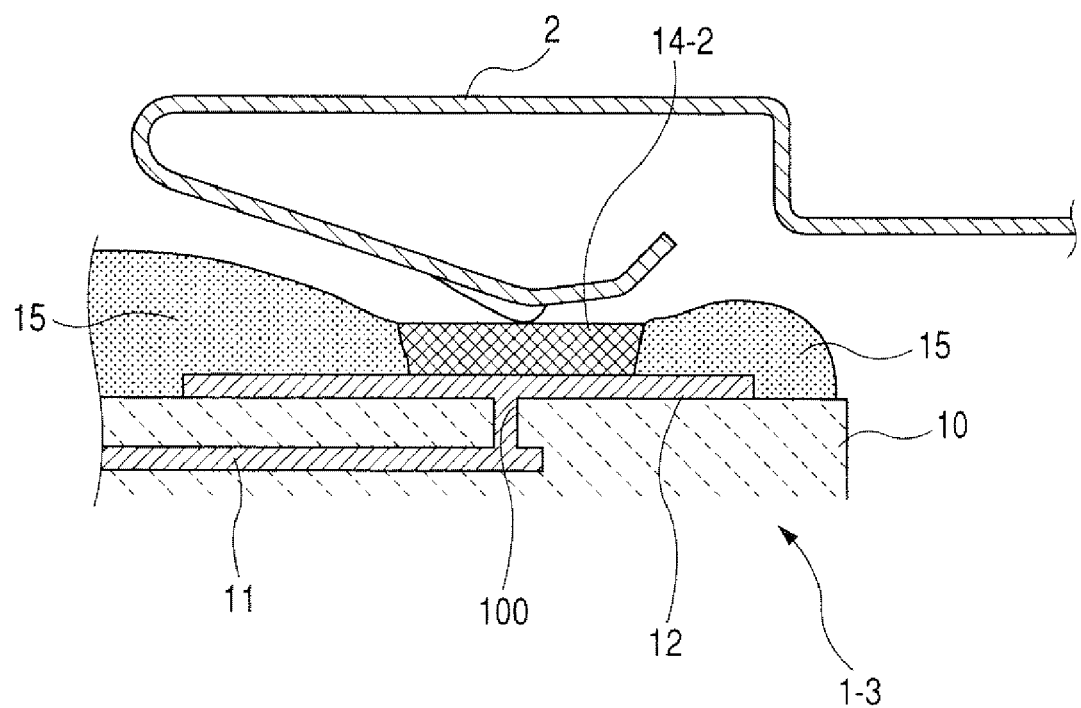
FIG. 6 shows a cross section of the contact area between the external electrode pad and the output terminal in the ceramic heater in its axial direction according to a fourth embodiment of the present invention.

FIG. 6 shows the cross section of the contact area between the external electrode pad 12 and the output terminal 2 in the ceramic heater 1-3, along its axial direction according to the fourth embodiment.

In the configuration of the ceramic heater 1-3 according to the fourth embodiment, a part of the outer peripheral surface of each external electrode pad 12 and its surrounding area are covered with the protective film 14-2 made of noble metal.

That is, the part of each external electrode pad 12, which is substantially connected to the output terminal 2, and the surrounding area of the part are covered with the protective film 14-2 made of noble metal. Other areas of the part in each external electrode pad 12 are covered with glass 15 made of silica as the main component.

The above construction of the ceramic heater 1-3 according to the fourth embodiment does not need to form the protective film on the entire of outer peripheral surface of each external electrode pad 12. It is thereby possible to decrease the manufacturing cost of the ceramic heater 1-3 with superior corrosion resistance and thermal resistance.

Other components of the ceramic heater 1-3 according to the fourth embodiment have the same configuration, action and effects of those in the ceramic heater according to the first embodiment shown in FIG. 1 to FIG. 3. The explanation for the same components is omitted here.

Fifth Embodiment

A description will be given of the gas sensor 4 equipped with the stacked type (or a lamination type) gas sensor element 3 according to the fifth embodiment of the present invention with reference to FIG. 7 to FIG. 9. The stacked type gas sensor element 3 is equipped with the ceramic heater according to one of the first to fourth embodiments.

Figure 7:
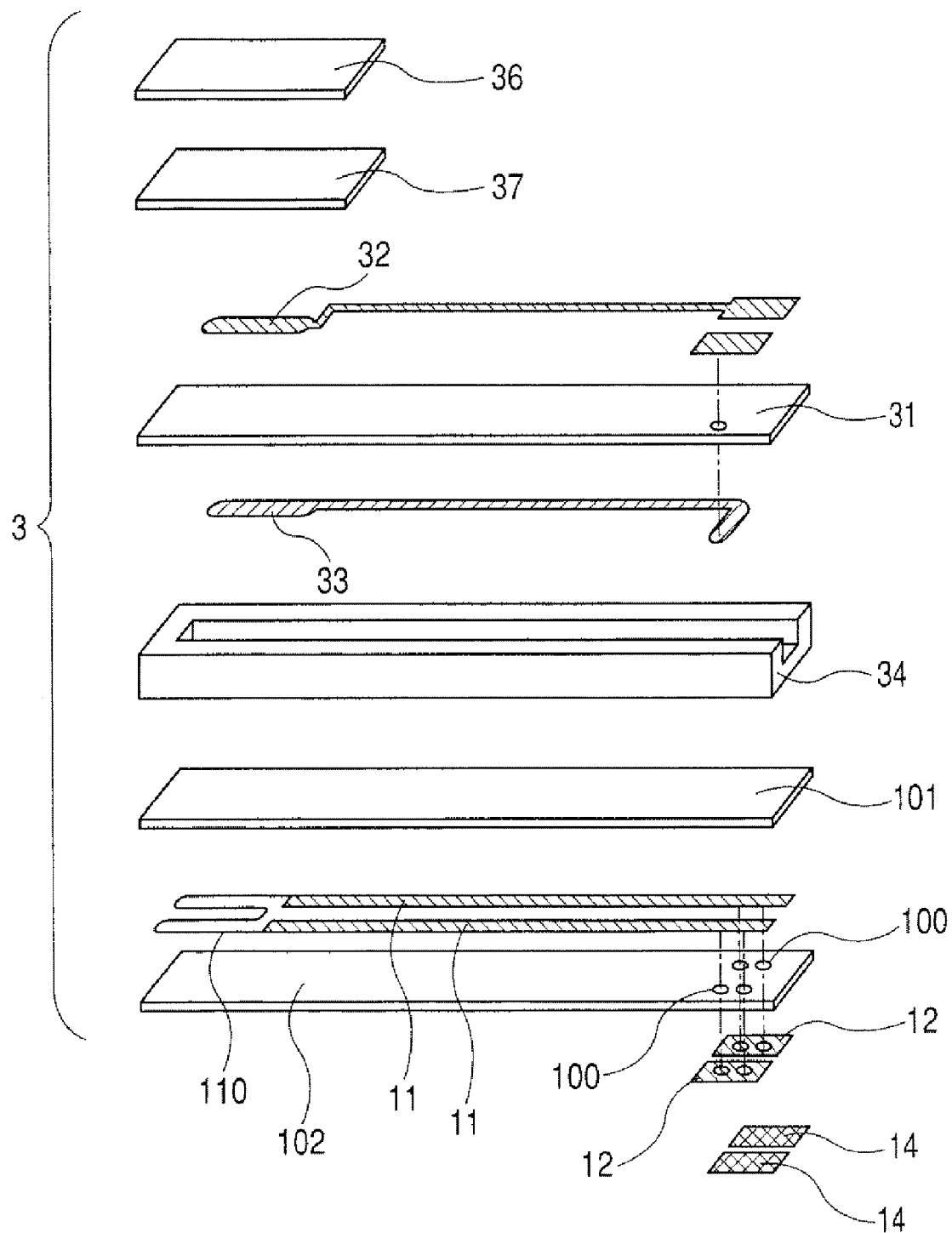
FIG. 7 is a diagram showing the construction of the gas sensor element that is built in the gas sensor according to the fifth embodiment of the present invention.

FIG. 7 shows the structure of the gas sensor element 3 to be built in the gas sensor 4 according to the fifth embodiment. FIG. 8 is the perspective diagram of the gas sensor element 3 shown in FIG. 7. FIG. 9 is the sectional diagram of the gas sensor 4 according to the fifth embodiment shown in FIG. 7 and FIG. 8.

Figure 9:
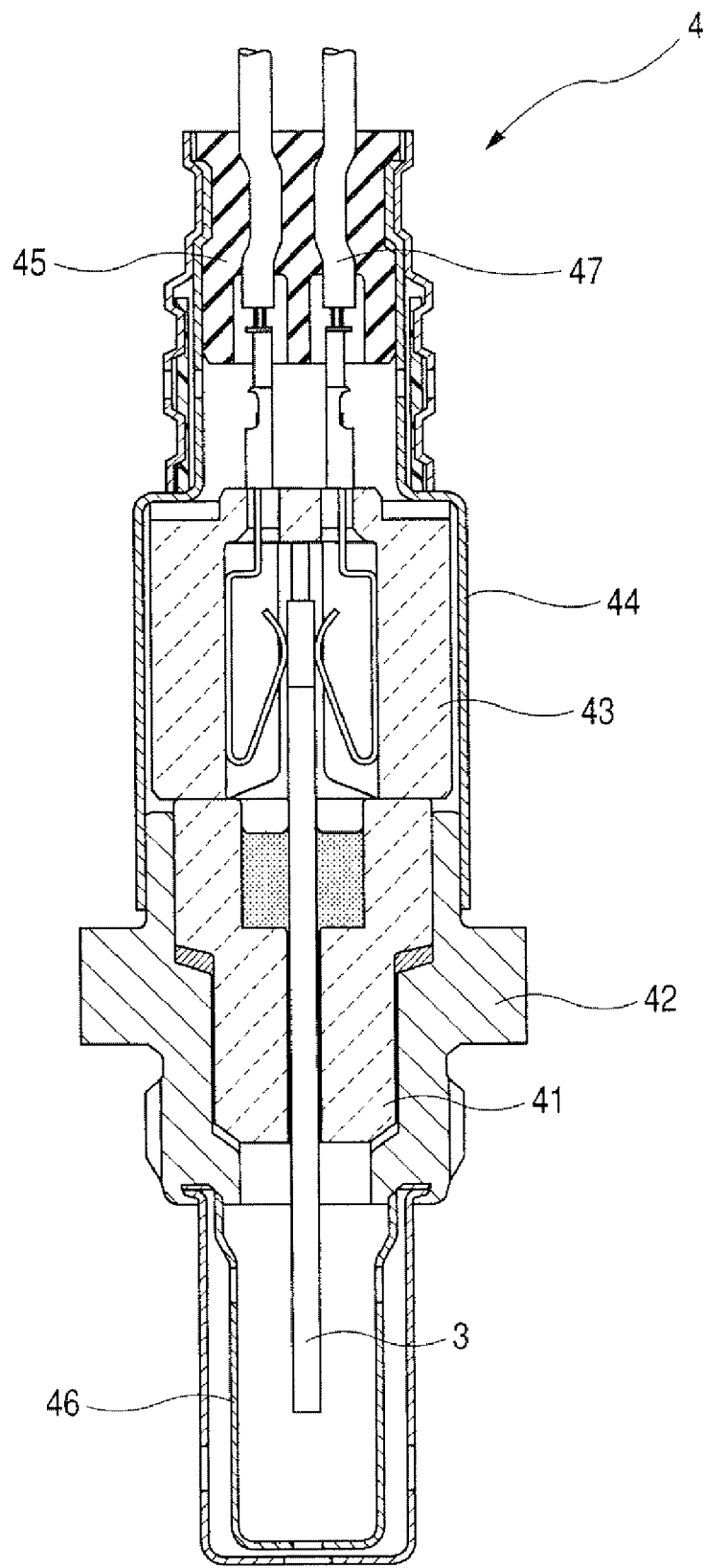
FIG. 9 is a sectional diagram of the stacked or lamination type gas sensor shown in FIG. 7 and FIG. 8 according to the fifth embodiment of the present invention.
Figure 10:
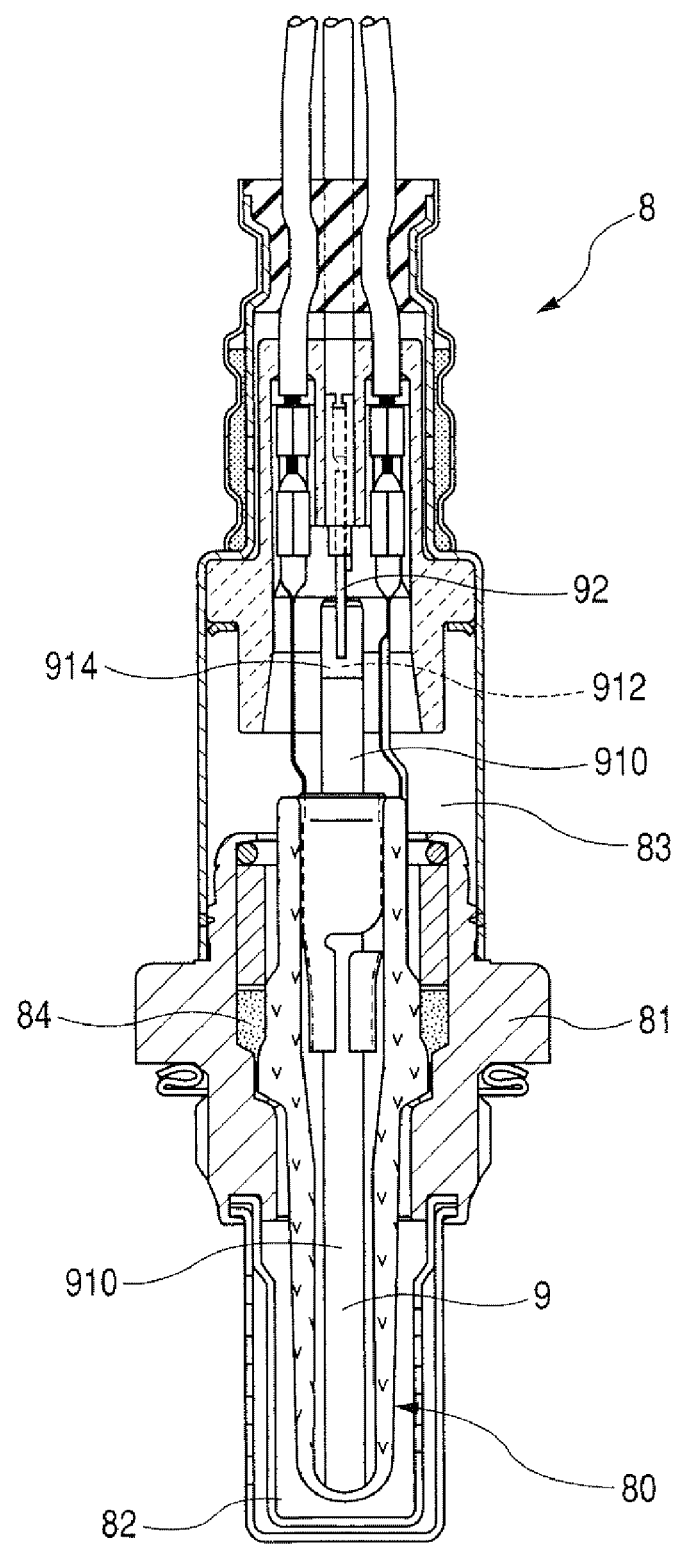
FIG. 10 is a sectional diagram of the gas sensor equipped with the conventional ceramic heater in its axial direction.

As shown in FIG. 9, the gas sensor 4 according to the fifth embodiment is comprised of the gas sensor element 3 equipped with the ceramic heater as one of the first to fourth embodiments, the element-side insulation glass 41, and the housing 42.

The gas sensor element 3 is inserted into the inside of and fitted to the element-side insulation glass 41. The housing 42 accommodates the element-side insulation glass 41.

The element cover 46 is disposed at the front end side of the housing 42 in order to protect the front end part of the gas sensor element 3. The atmosphere-side cover 44 is disposed at the base end part of the gas sensor element 3. The base end part of the gas sensor element 3 is covered with the atmosphere-side cover 44.

As shown in FIG. 7, the gas sensor element 3 in the gas sensor 4 according to the fifth embodiment is comprised of the solid electrolyte body 31, the target gas electrode 32, and the reference gas electrode 33. The solid electrolyte body 31 has oxygen ion conductivity. The target gas electrode 32 is disposed on one surface of the solid electrolyte body 31 in order to detect the target gas around that surface of the solid electrolyte body 31. The reference gas electrode 33 is disposed on the other surface of the solid electrolyte body 31.

The target gas electrode 32 is covered with the porous diffusion resistance layer 37 made of porous material and the dense shield layer 36.

The atmosphere chamber forming layer 34 is laminated (or stacked) on the surface of the solid electrolyte body 31 on which the reference gas electrode 33 is disposed. The atmosphere chamber forming layer 34 forms the atmosphere gas chamber into which atmosphere gas in introduced.

One of the ceramic heaters 1, 1-1, 1-2, and 1-3 according to the present invention shown in FIG. 1 to FIG. 6 is laminated or stacked on the atmosphere chamber forming layer 34.

As shown in FIG. 7, the ceramic heater has the primary heater member 101, the heating element 110, and the secondary heater member 102. The primary heater member 101 is adjacent to the atmosphere chamber forming layer 34. The heating element 110 is disposed on one surface of the primary heater member 101. The atmosphere chamber forming layer 34 is laminated on the other surface of the primary heater member 101. The heating element 110 is disposed between the primary heater member 101 and the secondary heater member 102.

The pair of external electrode pads 12 is disposed on one surface of the secondary heater member 102. The heating element 110 is disposed on the other surface of the secondary heater member 102.

The heating element 110 is electrically connected to the pair of external electrode pads 12 through the pair of heater leads 11 and the through holes 100. The pair of heater leads 11 is disposed in parallel in the longitudinal direction of the secondary heater member 102 on the surface of the secondary heater member 102.

The entire outer surface of each pair of the external electrode pads 12 is covered with the protective film 14 made of noble metal. Through the protective film 14, each external electrode pad 12 is electrically connected to the corresponding output terminal (omitted from FIG. 7) for the external lead.

Figure 8:
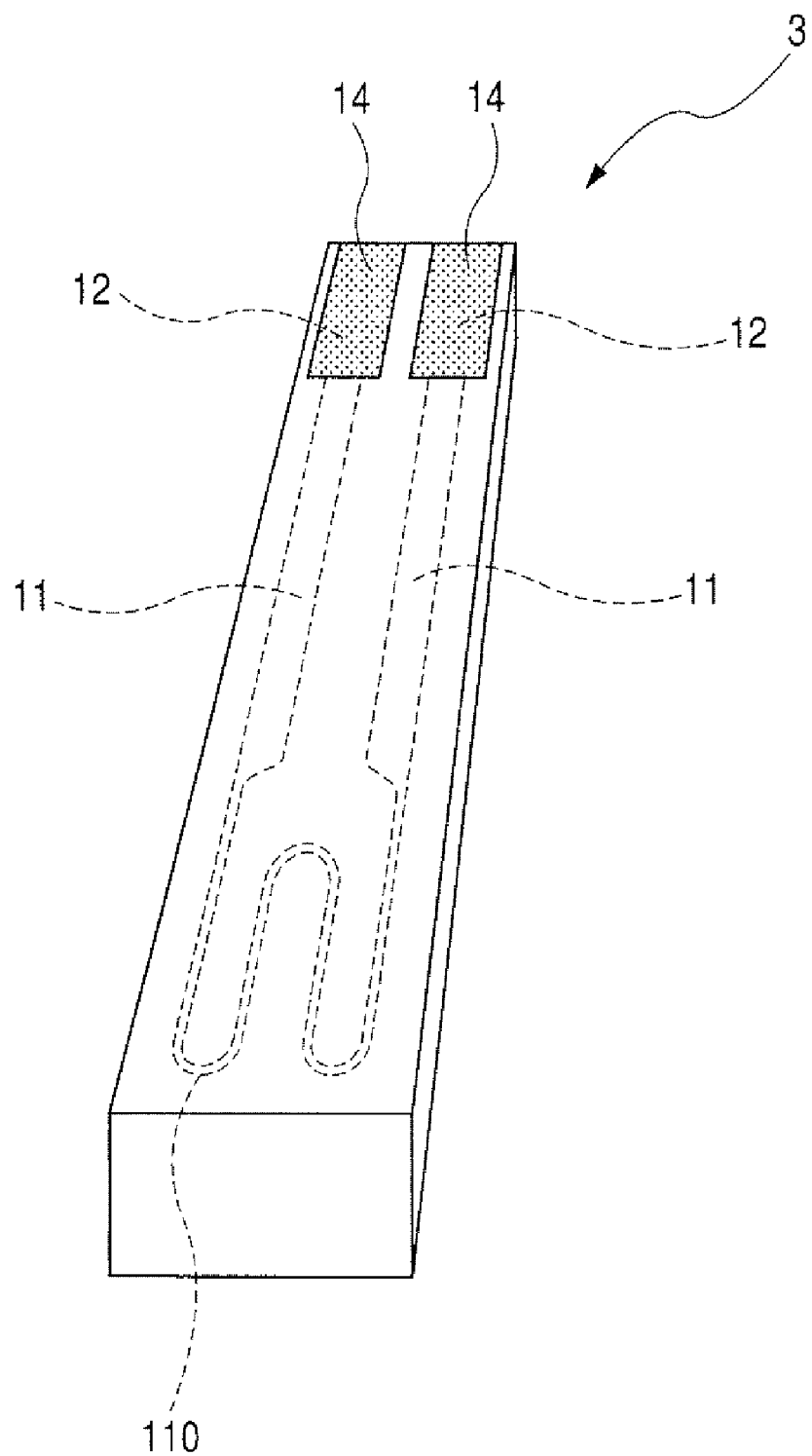
FIG. 8 is a perspective diagram of the gas sensor element shown in FIG. 7 that is built in the gas sensor according to the fifth embodiment of the present invention.

As described above in detail, it is possible to effectively show the action and effects of the present invention when the ceramic heater is built in the stacked type gas sensors having the structure shown in FIG. 7 and FIG. 8, for example.

Sixth Embodiment

A description will be given of the method of manufacturing the ceramic heater having the structure in which the pair of external electrode pads 12 are covered with the protective film 14 made of noble metal, as disclosed in the first embodiment shown in FIG. 1. The sixth embodiment uses the same reference numbers used in FIG. 1.

In the sixth embodiment, the Au plating film is formed as the primary plating layer on the outer surface of each external electrode pad 12 by performing electroless plating.

Next, heat treatment for the Au plating film is performed at a temperature of not less than 950°, more preferably, not less than 1064° C. which is the Au melting point.

Following this step, electro plating is carried out for the outer peripheral surface of the primary plating layer in order to form the secondary plating layer made of the Au plating film.

In the sixth embodiment, the plating is carried out twice in order to form the protective film 14 on the outer surface of the pair of external electrode pads 12. In particular, the primary plating layer as the inside plating layer of the protective film 14 is formed using electroless plating, and the secondary plating layer as the outside plating layer is formed using electro plating.

Although the sixth embodiment forms the double plating layer, it is possible to form a plurality of plating layers. In this modification, it is preferable to form at least one plating layer other than the most outside layer using electroless plating.

In the method according to the sixth embodiment, Au plating is carried out at a temperature of not less than 1064° C. which is the Au melting point. In the sixth embodiment, thermal treatment is carried out only after the formation of the primary plating layer. Such a thermal treatment can easily provide the ceramic heater 1 with superior corrosion resistance and thermal resistance. That is, after completion of the Au plating for the pair of external electrode pads 12, the thermal treatment is carried out for the Au plating film in order to soften Au material in the Au plating film. This enables the gold (Au) plating film to adequately adhere to the slightly rough surface of tungsten that forms the pair of external electrode pads 12.

That is, according to the method according to the sixth embodiment, it is possible to increase adhesion force generated between the external electrode pads 12 and the protective film 14 based on the Anchor effect. It is thereby possible to easily produce and provide the ceramic heater with superior corrosion resistance and thermal resistance.

Because the method of the sixth embodiment performs plating several times, even if pinholes are generated in each plating film it is possible to protect the protective film 14 composed of not less than two layers from completely penetrating any pinholes in the protective film 14.

Further, in the method of the sixth embodiment, the primary protective film 141 is formed by means of electroless plating. This step avoids the formation of non-plated area generated at the electrode contacts of the plating device when the plating is performed only using electro plating.

Still further, because the method of the sixth embodiment forms the secondary protective film 142 by means of electro plating, it is possible to form the dense outermost protective film in the primary protective film. This structure can suppress progress of abrasion at the contact points between the output terminals 2 and the protective film 14.

Seventh Embodiment

A description will be given of the method of manufacturing the ceramic heater having the protective film that is formed by means of paste printing. The seventh embodiment also uses the same reference numbers shown in FIG. 1.

In the seventh embodiment, a paste made by adding silica component into a paste containing noble metal is printed on the entire outer surface of each outer electrode pad 12. Following, the paste printed on the entire outer surface of each outer electrode pad 12 is burned so as to form the ceramic heater 1.

Specifically, in using a paste containing noble metal Pt, the paste printed on the entire outer surface of each outer electrode pad 12 is heated at a temperature within a range of 1100 to 1200° C.

It is possible for the ceramic heater produced using the method of the seventh embodiment to obtain the same action and effects of the ceramic heater according to the first to sixth embodiment of the present invention.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalent thereof.

What is claimed is:

1. A ceramic heater to be built in a gas sensor capable of detecting a concentration of a specific gas component contained in a target gas to be measured, comprising:
   a heater base member made of ceramic;
   a heating element formed in the inside of the heater base member;

a pair of external electrode pads, each of which is formed at an outer surface of the heater base member and electrically connected to a corresponding output terminal of an outer lead; and a pair of heater leads through which the heating element is electrically connected to a pair of the external electrode pads, wherein a pair of the external electrode pads, the heating element, and a pair of the heater leads are made of base metal, and at least a part of an outer surface of each external electrode pad is covered only with a dense protective film made only of noble metal, said noble metal being at least one of gold (Au), silver (Aq), platinum (Pt), rhodium (Rh), and palladium (Pd).

2. The ceramic heater according to claim 1, wherein the entire outer surface of each external electrode pad is covered with the dense protective film.

3. The ceramic heater according to claim 1, wherein the pair of the external electrode pads, the heating element, and the pair of the heater leads are made of tungsten (W).

4. A ceramic heater to be built in a gas sensor capable of detecting a concentration of a specific gas component contained in a target gas to be measured, comprising:

a heater base member made of ceramic;

a heating element formed in the inside of the heater base member;

a pair of external electrode pads, each of which is formed at an outer surface of the heater base member and electrically connected to a corresponding output terminal of an outer lead; and a pair of heater leads through which the heating element is electrically connected to a pair of the external electrode pads, wherein a pair of the external electrode pads, the heating element, and a pair of the heater leads are made of base metal, and at least a part of the outer surface of each external electrode pad is covered only with a dense protective film made solely of chromium (Cr).

5. The ceramic heater according to claim 4, wherein the entire outer surface of each external electrode pad is covered only with the dense protective film.

6. A gas sensor equipped with the ceramic heater according to claim 1.

* * * * *